United States Patent [19]

Clemens et al.

[11] Patent Number: 5,196,435

[45] Date of Patent: Mar. 23, 1993

[54] MELATONIN DERIVATIVES AND COMBINATIONS WITH ANTIESTROGEN COMPOUNDS FOR TREATING MAMMALIAN BREAST CARCINOMA

[75] Inventors: James A. Clemens; Michael E. Flaugh, both of Indianapolis, Ind.

[73] Assignee: Eli Lilly and Company, Indianapolis, Ind.

[21] Appl. No.: 796,108

[22] Filed: Nov. 21, 1991

[51] Int. Cl.$^5$ .................... A01N 43/38; A01N 43/42; A61K 31/44; A61K 31/405

[52] U.S. Cl. .................................... 514/284; 514/415; 514/419; 514/428; 514/514; 514/748; 514/771

[58] Field of Search ............... 514/284, 415, 419, 514, 514/428, 748, 751

[56] References Cited

U.S. PATENT DOCUMENTS

| | | | |
|---|---|---|---|
| 4,133,814 | 1/1979 | Jones et al. | 260/326.55 |
| 4,230,862 | 10/1980 | Suarez et al. | 546/237 |
| 4,418,068 | 11/1983 | Jones | 424/267 |
| 4,614,807 | 9/1986 | Flaugh | 548/507 |
| 4,623,660 | 11/1986 | Richardson | 514/514 |
| 4,855,305 | 8/1989 | Cohen | 514/415 |
| 4,943,572 | 7/1990 | von Angerer | 514/415 |
| 4,997,845 | 3/1991 | Flaugh | 514/415 |

FOREIGN PATENT DOCUMENTS 2512446 3/1983 France.

OTHER PUBLICATIONS

Blask, D. E., et al., *J. Neural. Transm.* [Suppl], 21: 433–449 (1986).
Blask, D. E., et al., *Neuroendocrinol. Lett.,* 9, No. 2: 63–731 (1987).
Abram, W. P. et al., *Br. J. Cancer,* 57: 604–607 (1988).

*Primary Examiner*—Nathan M. Nutter
*Attorney, Agent, or Firm*—Steven A. Fontana; Leroy Whitaker

[57] ABSTRACT

Derivatives of melatonin and the pharmaceutically acceptable salts thereof are useful for therapeutically treating hormonally dependent mammalian breast carcinoma. Combination treatments of melatonin derivatives and an antiestrogen compound are especially useful.

36 Claims, No Drawings

MELATONIN DERIVATIVES AND COMBINATIONS WITH ANTIESTROGEN COMPOUNDS FOR TREATING MAMMALIAN BREAST CARCINOMA

BACKGROUND OF THE INVENTION

Melatonin, represented by the structure below

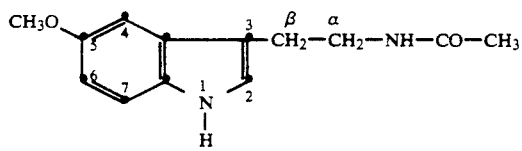

is named systematically as N-[2-(5-methoxy-3-indolyl)ethyl]acetamide. Trivial names for the compound include N-acetyl-5-methoxytryptamine and N-acetyl-O-methylserotonin. Melatonin is a pineal gland hormone which has ovulation inhibitory activity, Chu, et al., *Endocrinology*, 75: 238 (1964), as well as some activity against MCF-7 human breast cancer cells, Blask et al. *J. Neural. Transm.* [Supp.], 21: 433-449 (1986) and for the treatment of mammalian breast carcinoma, Blask, et al., *Neuroendocrinol. Lett.*, 9, No. 2: 63-73 (1987).

Several melatonin analogues of the formula

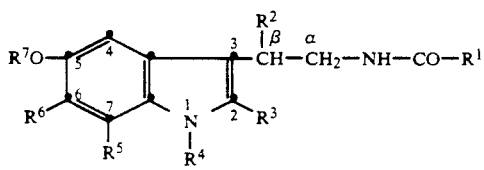

wherein
$R^1$ is H, $C_1$-$C_4$ alkyl, or $C_1$-$C_4$ alkoxy;
$R^2$ is H or $C_1$-$C_4$ alkyl;
$R^3$ is H or methyl;
$R^4$ is H, haloacetyl, $C_1$-$C_5$ alkanoyl, benzoyl, or benzoyl substituted with halo or methyl;
$R^5$ and $R^6$ are individually H or halo; and
$R^7$ is H or $C_1$-$C_4$ alkyl;
provided that when $R^2$ is H, at least one of $R^5$ and $R^6$ is halo; or when $R^5$ and $R^6$ are H, $R^2$ is $C_1$-$C_4$ alkyl, have also been prepared and have been shown to possess ovulation inhibition activity. See U.S. Pat. Nos. 4,997,845 and 4,614,807. However, none of these analogues were previously shown to possess activity against hormonally dependent mammalian breast carcinoma.

Tamoxifen (1-p-β-dimethylaminoethoxyphenyl-trans-1,2-diphenylbut-1-ene), represented by the structure

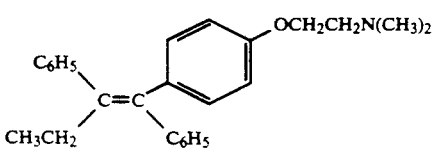

is a well-known antiestrogen compound having activity against mammalian breast carcinoma. See *The Merck Index*, 11th Ed., 1430 (1989). Furthermore, tamoxifen analogues also have antiestrogenic activity, including activity against mammalian breast carcinoma (U.S. Pat. No. 4,623,660). Numerous other compounds have similarly shown antiestrogenic activity resulting in suppression of mammalian breast tumor growth. For example, 2-phenyl-3-aroylbenzothiophenes and 2-phenyl-3-aroylbenzothiophene-1-oxides were disclosed in U.S. Pat. No. 4,133,814; 3-phenyl-4-aroyl-1,2-dihydronaphthalenes and 1-aroyl-2-phenylnaphthalenes were described in U.S. Pat. No. 4,230,862; and 6-hydroxy-2-(4-hydroxyphenyl)-3-[4-(2-piperidinoethoxy)benzoyl]benzo[b]thiophene was taught in U.S. Pat. No. 4,418,068.

Although tamoxifen has been studied in combination with cyclophosphamide as an intravenous injection, Abram et al., *Br. J. Cancer*, 57: 604-607 (1988), combinations of the above-mentioned melatonin analogues and antiestrogenic compounds, including tamoxifen, have not been tried for the treatment of hormonally dependent mammalian breast carcinoma.

It is the purpose of this invention to provide a method for the treatment of hormonally dependent mammalian breast carcinoma employing certain melatonin analogues. A further purpose of this invention provides a method for the treatment of hormonally dependent mammalian breast carcinoma employing a combination of certain melatonin analogues plus antiestrogen compounds which, when administered in adequate amounts, is synergistically effective against such carcinomas.

SUMMARY OF THE INVENTION

This invention provides a method of therapeutically treating hormonally dependent breast carcinoma in a mammal which comprises administering to said mammal an effective amount of a compound of the formula

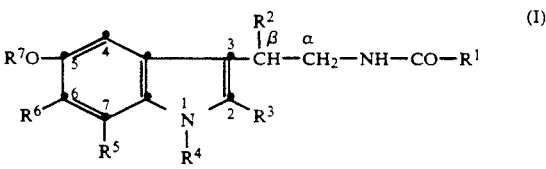

wherein
$R^1$ is H, $C_1$-$C_4$ alkyl, or $C_1$-$C_4$ alkoxy;
$R^2$ is H or $C_1$-$C_4$ alkyl;
$R^3$ is H or methyl;
$R^4$ is H, haloacetyl, $C_1$-$C_5$ alkanoyl, benzoyl, or benzoyl substituted with halo or methyl;
$R^5$ and $R^6$ are individually H or halo;
$R^7$ is H or $C_1$-$C_4$ alkyl;
provided that when $R^2$ is H, at least one of $R^5$ and $R^6$ is halo; or when $R^5$ and $R^6$ are H, $R^2$ is $C_1$-$C_4$ alkyl; or a pharmaceutically acceptable salt thereof.

Preferred compounds of the above formula include β-methyl-6-fluoromelatonin, β-ethyl-6-chloromelatonin and 2-methyl-6,7-dichloromelatonin. β-methyl-6-chloromelatonin is especially preferred. With each of these melatonin derivatives, $R^1$ and $R^7$ are methyl.

This invention also provides a method of therapeutically treating hormonally dependent breast carcinoma in a mammal which comprises administering to said mammal an effective amount of a first component which is a compound of the above formula (I), or a pharmaceutically acceptable salt thereof, and an effective amount of a second component which is an antiestrogen compound or a pharmaceutically acceptable salt thereof. With this method of treating such mammalian breast carcinomas, preferred first component compounds include β-methyl-6-fluoromelatonin, β-ethyl-6-chloromelatonin and 2-methyl-6,7-dichloromelatonin while β-methyl-6-chloromelatonin is especially preferred. Preferred second component antiestrogen compounds include nonsteroidal, antiestrogenic compounds, and tamoxifen is especially preferred.

Further provided in this invention is a method of therapeutically treating hormonally dependent breast carcinoma in a mammal which comprises administering to said mammal a first component which is a compound of the above formula (I), or a pharmaceutically acceptable salt thereof, and a second component which is an antiestrogen compound or a pharmaceutically acceptable salt thereof; said first and second component being administered in amounts which are synergistically effective against said breast carcinoma. Preferred and especially preferred first and second component compounds are as specified above.

Also contemplated within the scope of this invention is a method of therapeutically treating hormonally dependent breast carcinoma in a mammal which comprises administering to said mammal an effect amount of a first component which is a compound of the above formula (I), or a pharmaceutically acceptable salt thereof, and an effective amount of a second component which is an antiestrogen compound, or a pharmaceutically acceptable salt thereof; wherein said first component and said second component, together with a pharmaceutically acceptable diluent, excipient or carrier, forms a pharmaceutical formulation for said administration. Preferred and especially preferred first and second components, as specified above, are the same for this pharmaceutical formulation.

DETAILED DESCRIPTION OF THE INVENTION

The following definitions refer to the various terms used above and throughout the disclosure.

The term "halo" refers to fluoro, chloro, bromo, and iodo.

The term "$C_1$-$C_4$ alkyl" or "lower alkyl" refers to the straight and branched aliphatic radicals of 1–4 carbon atoms including methyl, ethyl, propyl, isopropyl, n-butyl, isobutyl, sec-butyl, and tert-butyl.

The terms "$C_1$-$C_4$ alkoxy" includes the straight and branched aliphatic ether radicals of 1–4 carbon atoms such as methoxy, ethoxy, propoxy, isopropoxy, n-butoxy, isobutoxy, sec-butoxy, and tert-butoxy.

The term "halocetyl" refers to chloroacetyl, bromoacetyl, fluoroacetyl, and iodoacetyl.

The term "$C_1$-$C_5$ alkanoyl" includes formyl, acetyl, propionyl, butyryl, α-methylpropionyl, valeryl, α-methylbutyryl, β-methylbutyryl, and pivaloyl.

The term "benzoyl substituted with halo" defines mono- and di-halo benzoyl groups. Specific mono-halo benzoyl groups are chlorobenzoyl, bromobenzoyl, fluorobenzoyl, and iodobenzoyl.

Di-halo benzoyl groups include those in which both halo substituents are the same. Typical di-halo benzoyl groups include 2,4-dichlorobenzoyl, 2,4-dibromobenzoyl, 2,4-difluorobenzoyl, and 2,4-diiodobenzoyl.

The term "benzoyl substituted with methyl" contemplates methylbenzoyl, dimethylbenzoyl, and trimethylbenzoyl.

The term "heterocyclic radical" includes a 5- or 6-membered nitrogen-containing ring structures optionally including an oxygen or sulfur atom as a second hetero-atom. Typically substituted heterocyclic radicals include pyrrolidino, piperidino, and morpholino.

The compounds employed in the method of this invention are known in the art or can be made by methods described in the art. In general, the compounds of formula (I) are known as ovulation inhibitors. Representative publications which teach the preparation of the compounds of formula (I) include, but are not limited to, U.S. Pat. Nos. 4,614,807 and 4,997,845.

While all of the compounds of formula (I) are believed to be useful for treating hormonally dependent mammalian breast carcinoma, certain of these compounds are preferred for such use. Preferred $R^2$ substituents for the compounds of formula (I) are $C_1$-$C_4$ alkyl, especially methyl. Preferred $R^5$ and $R^6$ substituents are halo wherein $R^5$ or $R^6$ is individually halo and the other is hydrogen, or both may be substituted with the same halogen atom, especially chloro. An especially preferred compound of formula (I) is where $R^1$ and $R^2$ are methyl; $R^3$, $R^4$ and $R^5$ are hydrogen; $R^6$ is chloro; and $R^7$ is methyl.

The compounds of formula (I), as used in this invention, are useful in therapeutically treating hormonally dependent mammalian breast carcinoma when administered in an effective amount. The term "therapeutically treating hormonally dependent breast carcinoma", as employed in the specification of this application, including the claims, is to be construed as any means which adversely affect the existence or growth of breast carcinoma in mammals. The term "effective amount" means that dosage of active substance sufficient to provide therapeutical treatment of mammalian breast carcinoma.

The term "hormonally dependent carcinoma" is generally understood in the art to mean those carcinomas in which the growth thereof is influenced, in any manner, by the presence, absence, abundance or insufficiency of mammalian hormones. Such hormones include but are not limited to estrogen and prolactin. However, it is important to recognize that the mechanism of action of the compounds of formula (I) is directly against carcinoma tissue. Thus, the mechanism of action of the compounds of formula (I) is neither hormonal nor antihormonal, so these compounds provide a distinct mechanism of action for treating breast carcinoma.

Compounds referred to as antiestrogenic, including their composition, use and preparation, are also well known in the art. The following publications are representative but by no means exclusive of references which teach the composition, preparation and use of antiestrogen compounds: U.S. Pat. Nos. 4,133,814, 4,230,862, 4,418,068, and 4,623,660 and *The Merck Index* 11th Ed. (1989), and *Cytotoxic Estrogen in Hormone Receptive Tumors* (J. Raus, et al. 1980).

When used in combination with the compounds of formula (I), all antiestrogenic compounds are believed to be useful for treating mammalian breast carcinoma. Particularly useful are non-steroidal antiestrogen compounds, including the alkene derivatives of the formula

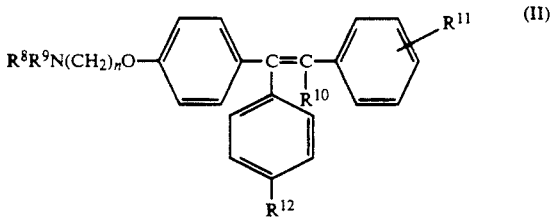

(II)

methyl-6-chloromelatonin and tamoxifen is especially preferred.

Treatments in which a first and a second component compound are administered to the same mammal having a breast carcinoma are frequently synergistically effective against such a carcinoma. Data in Table 1 provide evidence of this synergistic effect. A description of experimental procedures appears below.

TABLE 1

EFFECT OF ORALLY ADMINISTERED
β-METHYL-6-FLUOROMELATONIN, WITH AND WITHOUT TAMOXIFEN,
ON GROWTH OF DMBA-INDUCED MAMMARY TUMORS

| Week of Treatment | Average Tumor Area (mm$^2$)$\bar{x}$ ± SEM$^a$ | | | |
|---|---|---|---|---|
| | Vehicle Corn Oil 0.2 ml Oral | β-methyl-6-fluoro-melatonin 15 mg/kg | Tamoxifen Citrate 5 mg/kg | β-methyl-6-fluoro-melatonin + Tamoxifen Citrate |
| Start | 27.4 ± 2.6 | 24.6 ± 2.9 | 21.6 ± 1.7 | 25.1 ± 2.0 |
| 1 | 103.9 ± 9.8 | 81.7 ± 8.1 | 43.1 ± 5.1* | 37.6 ± 5.0* |
| 2 | 332.0 ± 54.8 | 116.3 ± 23.1* | 37.1 ± 23.1* | 4.6 ± 3.0* |
| 3 | 617.1 ± 92.0 | 166.0 ± 40.5* | 91.4 ± 65.3* | 0.0 ± 0* |
| 4 | 860.2 ± 59.7 | 261.5 ± 72.8* | 147.0 ± 105* | 2.3 ± 2.3* |

$^a$Each test group contained 7 rats.
*Significantly different from control (P < .05).

wherein
either $R^8$ is H or a lower alkyl radical and $R^9$ is a lower alkyl radical, or $R^8$ and $R^9$ are joined together with the adjacent nitrogen atom to form a heterocyclic radical;
$R^{10}$ is H or a lower alkyl radical;
$R^{11}$ is H, halo, OH, a lower alkyl radical, or is a buta-1,3-dienyl radical which together with the adjacent benzene ring forms a naphthyl radical;
$R^{12}$ is H or OH;
n is 2;
or a pharmaceutically acceptable salt thereof. Preferred formula (II) compounds are when $R^8$ and $R^9$ are both the same lower alkyl radical, especially methyl; $R^{10}$ is a lower alkyl radical, especially ethyl; $R^{11}$ is halo, especially fluorine, chlorine or bromine, or $R^{11}$ is a lower alkyl radical, especially methyl or ethyl; $R^{12}$ is OH; and n is 2. The compounds of formula (II) are otherwise known as analogs of another antiestrogen compound, tamoxifen, which is especially preferred.

Preferred combinations of compounds of formula (I), referred to as first components, and antiestrogen compounds, referred to as second components, for therapeutically effective treatment of hormonally dependent mammalian breast carcinoma include β-methyl-6-fluoromelatonin or 2-methyl-6,7-dichloromelatonin, or β-ethyl-6-chloromelatonin and tamoxifen, while β-

However, synergism between a first component compound of formula (I) and a second component antiestrogen compound is not always demonstrable in side-by-side comparisons. When first or second component compounds individually exhibit such a high level of activity on mammary tumors that significant differences between an individual treatment and a combination treatment does not exist, the synergistic effect of the combination treatment of first and second component compounds is not demonstrable. (Table 2).

TABLE 2

EFFECT OF ORALLY ADMINISTERED
β-METHYL-6-FLUOROMELATONIN, WITH AND WITHOUT TAMOXIFEN,
ON GROWTH OF DMBA-INDUCED MAMMARY TUMORS

| Week of Treatment | Average Tumor Area (mm$^2$)$\bar{x}$ ± SEM$^a$ | | | |
|---|---|---|---|---|
| | Vehicle Corn Oil 0.2 ml Oral | β-methyl-6-fluoro-melatonin 15 mg/kg | Tamoxifen Citrate 5 mg/kg | β-methyl-6-fluoro-melatonin + Tamoxifen Citrate |
| Start | 24.3 ± 2.5 | 26.4 ± 1.8 | 25.1 ± 2.5 | 25.9 ± 2.4 |
| 1 | 80.3 ± 8.4 | 48.0 ± 6.2* | 30.3 ± 5.1* | 31.0 ± 7.5* |
| 2 | 202.6 ± 17.3 | 78.9 ± 10.3* | 15.0 ± 6.7* | 26.7 ± 16.8* |
| 3 | 540.0 ± 121 | 76.7 ± 22.5* | 5.9 ± 3.9* | 41.1 ± 35.3* |
| 4 | 1046.0 ± 348 | 138.3 ± 46.2* | 5.1 ± 3.4* | 41.1 ± 35.3* |

$^a$Each test group contained 7 rats.
*Significantly different from control (P < .05).

When used in combination, first component compounds and second component compounds may be independently prepared as pharmaceutical formulations for administration to mammals, or first and second component compounds may be combined and then further combined with a pharmaceutically acceptable diluent, excipient or carrier to form a pharmaceutical formulation for administration. The former method of pharmaceutical formulation preparation and administration is preferred.

As will be recognized by those skilled in the art, many of the compounds used in this invention contain an asymmetric carbon atom. This invention is not limited to any particular isomer but includes the individual enantiomers as well as the racemates of the compounds.

The pharmaceutically acceptable acid addition salts used in this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caparate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluene-sulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

DMBA-Induced Mammary Tumor Inhibition

Mammary tumors were produced in female Sprague-Dawley rats which were purchased from Harlan Industries, Indianapolis, Ind. At about 55 days of age, the rats received a single oral feeding of 20 mg of 7,12-dimethylbenz[a]anthracene (DMBA). About 6 weeks after DMBA administration, the mammary glands were palpated at weekly intervals for the appearance of tumors. Whenever one or more tumors appeared, the longest and shortest diameters of each tumor were measured with a metric caliper, the measurements were recorded, and that animal was selected for experimentation. An attempt was made to uniformly distribute the various sizes of tumors in the treated and control groups such that average-sized tumors were equivalently distributed between test groups. Control groups and test groups for each experiment contained 5 to 9 animals. The average number of test animals is stated for each experiment in the data tables contained herein.

Test compounds were administered either through intraperitoneal injections in 2% acacia, or orally. Orally administered compounds were either dissolved or suspended in 0.2 mL corn oil. Each treatment, including acacia and corn oil control treatments, was administered once daily to each test animal. Following the initial tumor measurement and selection of test animals, tumors were measured each week by the above-mentioned method. The treatment and measurements of animals continued for 3 to 5 weeks at which time the final areas of the tumors were determined. For each compound and control treatment, the change in the mean tumor area was determined. The mean change was analyzed for its significance, using Student's t-test. The results of these tests are shown in Tables 3 through 7 below.

TABLE 3

EFFECT OF IP-ADMINISTERED $\beta$-METHYL-6-CHLOROMELATONIN AND 2-METHYL-6,7-DICHLOROMELATONIN ON GROWTH OF DMBA-INDUCED MAMMARY TUMORS

| Week of Treatment IP[b] | Average Tumor Area (mm$^2$)x ± SEM[a] | | | |
|---|---|---|---|---|
| | Vehicle Acacia | Melatonin 15 mg/kg | $\beta$-methyl-6-chloro-melatonin 15 mg/kg | 2-methyl-6,7-dichloro-melatonin 15 mg/kg |
| Start | 47.9 ± 3.6 | 44.1 ± 5.1 | 47.7 ± 7.0 | 34.3 ± 5.7 |
| 1 | 106.0 ± 10.4 | 90.0 ± 8.6 | 78.6 ± 7.5* | 88.0 ± 12.9 |
| 2 | 236.1 ± 33.8 | 159.1 ± 21.4 | 118.4 ± 18.9* | 152.7 ± 31.0 |
| 3 | 565.3 ± 105 | 333.4 ± 65.3 | 142.7 ± 26.0* | 259.3 ± 41.7* |
| 4 | 915.7 ± 63.5 | 599.3 ± 205 | 237.5 ± 40.1* | 402.0 ± 87.3* |

[a]Each test group contained 7 rats
[b]IP = intraperitoneal administration of test compounds in 2% acacia.
*Significantly different from control (P < 0.05).

TABLE 4

EFFECT OF ORALLY ADMINISTERED $\beta$-ETHYL-6-CHLOROMELATONIN ON GROWTH OF DMBA-INDUCED MAMMARY TUMORS

| Week of Treatment | Average Tumor Area (mm$^2$)x ± SEM[a] | |
|---|---|---|
| | Vehicle Corn Oil 0.2 ml Oral | $\beta$-ethyl-6-chloromelatonin 15 mg/kg Oral |
| Start | 22.5 ± 1.5 | 23.9 ± 1.8 |
| 1 | 109.3 ± 12 | 54.5 ± 11* |
| 2 | 255.7 ± 37 | 71.5 ± 22* |
| 3 | 580.0 ± 110 | 81.7 ± 32* |
| 4 | 768.0 ± 79 | 103.0 ± 40* |

[a]The acacia test group contained 6 rats and the $\beta$-ethyl-6-chloromelatonin test group contained 8 rats.
*Significantly different from control (P < 0.05).

TABLE 5

EFFECT OF ORALLY ADMINISTERED $\beta$-METHYLMELATONIN, $\beta$-ETHYL-6-CHLOROMELATONIN AND $\beta$-DIMETHYL-6-CHLOROMELATONIN ON GROWTH OF DMBA-INDUCED MAMMARY TUMORS

| Week of Treatment | Average Tumor Area (mm$^2$)x ± SEM[a] | | | |
|---|---|---|---|---|
| | Vehicle Corn Oil Oral | $\beta$-methyl-melatonin 15 mg/kg | $\beta$-ethyl-6-chloro-melatonin 15 mg/kg | $\beta$-dimethyl-6-chloro-melatonin 15 mg/kg |
| Start | 24.1 ± 2.1 | 27.3 ± 3.3 | 20.3 ± 1.4 | 24.0 ± 1.3 |
| 1 | 88.1 ± 14.6 | 87.7 ± 17.9 | 42.1 ± 5.8* | 65.9 ± 12.2 |
| 2 | 206.0 ± 32.5 | 176.3 ± 41.7 | 91.4 ± 18.5* | 152.6 ± 33.3 |
| 3 | 572.0 ± 102 | 467.0 ± 143 | 179.0 ± 53* | 406.0 ± 102 |

[a]Each test group contained 7 rats.
*Significantly different from control (P < 0.05)

TABLE 6
EFFECT OF ORALLY ADMINISTERED β-METHYL-6-FLUOROMELATONIN ON GROWTH OF DMBA-INDUCED MAMMARY TUMORS

| Week of Treatment | Average Tumor Area (mm$^2$)x ± SEM$^a$ | |
|---|---|---|
| | Vehicle Corn Oil 0.2 ml Oral | β-methyl-6-fluoro-melatonin 15 mg/kg |
| Start | 22.6 ± 1.5 | 23.3 ± 1.4 |
| 1 | 108.9 ± 7.3 | 58.1 ± 12.6* |
| 2 | 227.4 ± 30.3 | 174.0 ± 106 |
| 3 | 438.9 ± 68.2 | 205.0 ± 160 |
| 4 | 692.0 ± 73.3 | 313.0 ± 260 |

$^a$Each test group contained 9 rats.
*Significantly different from control (P < .05).

TABLE 7
EFFECT OF ORALLY ADMINISTERED β-METHYL-6-FLUOROMELATONIN ON GROWTH OF DMBA-INDUCED MAMMARY TUMORS

| Week of Treatment | Average Tumor Area (mm$^2$)x ± SEM$^a$ | |
|---|---|---|
| | Vehicle Corn Oil 0.2 ml Oral | β-methyl-6-fluoro melatonin 15 mg/kg |
| Start | 28.1 ± 2.6 | 27.9 ± 2.3 |
| 1 | 102.4 ± 11.0 | 81.3 ± 13.7 |
| 2 | 308.9 ± 45.0 | 71.9 ± 22.3* |
| 3 | 258.4 ± 39.6 | 243.6 ± 96.2 |
| 4 | 393.0 ± 150 | 317.0 ± 190 |
| 5 | 456.0 ± 234 | 183.0 ± 117 |

$^a$Each test group contained 7 rats.
*Significantly different from control (P < .05).

For therapeutic treatment of hormonally dependent mammalian breast carcinoma, the compounds of formula (I), with or without an antiestrogen compound, may be administered as such, or they can be compounded and formulated into pharmaceutical compositions in unit dosage form for parenteral or intraveneous administration or, preferably, oral administration. Such pharmaceutical compositions are prepared in a manner well known in the art and comprise at least one active compound of the above formula (I), optionally including a compound having antiestrogenic activity, associated with a pharmaceutically carrier. In such a composition, the active compound and, if included, the antiestrogen compound, are known as active ingredients. In making the compositions, the active ingredient(s) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tables, pills, powders, lozenges, sachets, cachets, elixirs, emulsions, solutions, syrups, suspensions, soft and hard gelatin capsules, sterile injectable solutions, and sterile packaged powders. Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art. For oral administration, a compound of formula (I), optionally including a compound having antiestrogenic activity, can be addmixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects and other mammals, each unit containing a predetermined quantity of active material calculated to produce the desired therapeutic effect, in association with the required pharmaceutical carrier. Such compositions may contain a compound of formula (I) as an active ingredient or may contain a compound of formula (I) plus an antiestrogen compound as active ingredients.

The active compounds of formula (I) are effective over a wide dosage range. For example, daily dosages will normally fall within the range of about 0.1 mg/kg to about 50 mg/kg of body weight. In the treatment of adult humans, the dosage range from about 5 mg/kg to about 25 mg/kg, in single or divided doses, is preferred. However, it will be understood that the amount of the compound actually administered will be determined by a physician in light of the relevant circumstances including the relative severity of the breast carcinoma, the choice of compound or compounds to be administered, the age, weight, and response of the individual patient, and the chosen route of administration. Therefore, the above dosage ranges are not intended to limit the scope of this invention in any way. Dosage ranges for antiestrogen compounds are known in the art and should be used accordingly.

We claim:

1. A method of therapeutically treating hormonally dependent breast carcinoma in a mammal in need of such treatment which comprises administering to said mammal an effective amount of a compound of the formula

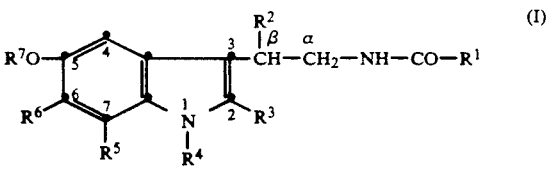

wherein
$R^1$ is H, $C_1-C_4$ alkyl, or $C_1-C_4$ alkoxy;
$R^2$ is H or $C_1-C_4$ alkyl;
$R^3$ is H or methyl;
$R^4$ is H, haloacetyl, $C_1-C_5$ alkanoyl, benzoyl, or benzoyl substituted with halo or methyl;
$R^5$ and $R^6$ are individually H or halo;
$R^7$ is H or $C_1-C_4$ alkyl;
provided that when $R^2$ is H, at least one of $R^5$ and $R^6$ is halo; or when $R^5$ and $R^6$ are H, $R^2$ is $C_1-C_4$ alkyl; or a pharmaceutically acceptable salt thereof.

2. A method according to claim 1, wherein $R^2$ of said compound is $C_1-C_4$ alkyl.

3. A method according to claim 1, wherein $R^5$ or $R^6$ of said compound is individually halo and the other is H.

4. A method according to claim 3, wherein $R^6$ is halo.

5. A method according to claim 4, wherein said halo is chloro.

6. A method according to claim 1, wherein said compound is β-methyl-6-chloromelatonin.

7. A method according to claim 1, wherein said compound is 2-methyl-6,7-dichloromelatonin.

8. A method according to claim 1, wherein said compound is β-methyl-6-fluoromelatonin.

9. A method according to claim 1, wherein said mammal is a human.

10. A method of therapeutically treating hormonally dependent breast carcinoma in a mammal in need of such treatment which comprises administering to said mammal an effective amount of a first component which is a compound of the formula

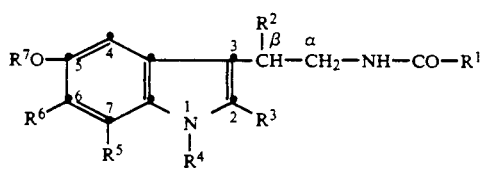

wherein
$R^1$ is H, $C_1$-$C_4$ alkyl, or $C_1$-$C_4$ alkoxy;
$R^2$ H or $C_1$-$C_4$ alkyl;
$R^3$ is H or methyl;
$R^4$ is H, haloacetyl, $C_1$-$C_5$ alkanoyl, benzoyl, or benzoyl substituted with halo or methyl;
$R^5$ and $R^6$ are individually H and halo;
$R^7$ is H or $C_1$-$C_4$ alkyl:
provided that when $R^2$ is H, at least one of $R^5$ and $R^6$ is halo; or when $R^5$ and $R^6$ are H, $R^2$ is $C_1$-$C_4$ alkyl; or a pharmaceutically acceptable salt thereof, and an effective amount of a second component which is an antiestrogen compound or a pharmaceutically acceptable salt thereof.

11. A method according to claim 10, wherein $R^2$ of said compound is $C_1$-$C_4$ alkyl.

12. A method according to claim 10, wherein $R^5$ or $R^6$ of said compound is individually halo and the other is H.

13. A method according to claim 10, wherein said first component is β-methyl-6-chloromelatonin.

14. A method according to claim 10, wherein said first component is 2-methyl-6,7-dichloromelatonin.

15. A method according to claim 10, wherein said first component is β-methyl-6-flouromelatonin.

16. A method according to claim 10, wherein said second component is tamoxifen.

17. A method according to claim 13, wherein said second component is tamoxifen.

18. A method according to claim 14, wherein said second component is tamoxifen.

19. A method according to claim 15, wherein said second component is tamoxifen.

20. A method according to claim 10, wherein said second component is an alkene derivative of the formula

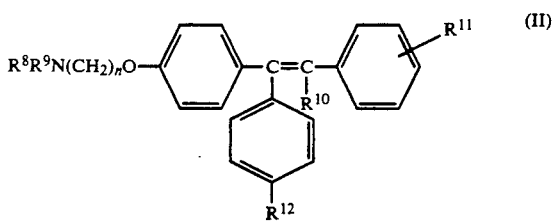

wherein
either $R^8$ is H or $C_1$-$C_4$ alkyl and $R^9$ is $C_1$-$C_4$ alkyl, or $R^8$ and $R^9$ are joined together with the adjacent nitrogen atom to form a heterocyclic radical, wherein said heterocyclic radical is a 5- or 6-membered nitrogen-containing ring structure optionally including an oxygen or sulfur atom as a second hetero-atom;
$R^{10}$ is H or $C_1$-$C_4$ alkyl;
$R^{11}$ is H, halo, OH, $C_1$-$C_4$ alkyl, or is a buta-1,3-dienyl radical such that together with the adjacent benzene ring forms a naphthyl radical;
$R^{12}$ is H or OH;
n is 2;
or a pharmaceutically acceptable salt thereof.

21. A method according to claim 20, wherein $R^8$ and $R^9$ of said alkene derivative are both the same $C_1$-$C_4$ alkyl group;
$R^{10}$ is $C_1$-$C_4$ alkyl;
$R^{11}$ is halo or $C_1$-$C_4$ alkyl;
$R^{12}$ is OH; and
n is 2.

22. A method according to claim 10, wherein said first component and said second component, together with a pharmaceutically acceptable diluent, excipient or carrier, form a pharmaceutical formulation for said administration.

23. A method according to claim 10, wherein said mammal is a human.

24. A method of therapeutically treating hormonally dependent breast carcinoma in a mammal in need of such treatment which comprises administering to said mammal a first component which is a compound of the formula

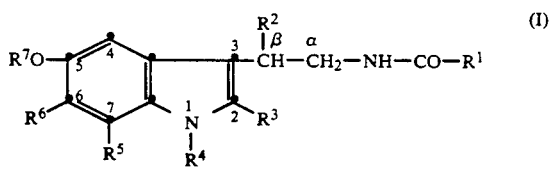

wherein
$R^1$ is H, $C_1$-$C_4$ alkoxy;
$R^2$ is H or $C_1$-$C_4$ alkyl;
$R^3$ is H or methyl;
$R^4$ is H, haloacetyl, $C_1$-$C_5$ alkanoyl, benzoyl, or benzoyl substituted with halo or methyl;
$R^5$ and $R^6$ are individually H or halo; and
$R^7$ is H or $C_1$-$C_4$ alkyl;
provided that when $R^2$ is H, at least one of $R^5$ and $R^6$ is halo; or when $R^5$ and $R^6$ are H, $R^2$ is $C_1$-$C_4$ alkyl; or a pharmaceutically acceptable salt thereof, and a second component which is an antiestrogen compound or a pharmaceutically acceptable salt thereof; said first and second component being administered in amounts which are synergistically effective against said breast carcinoma.

25. A method according to claim 24, wherein $R^2$ of said compound is $C_1-C_4$ alkyl.

26. A method according to claim 24, wherein R5 or R6 of said compound is individually halo and the other is H.

27. A method according to claim 24, wherein said first component is β-methyl-6-chloromelatonin.

28. A method according to claim 24, wherein said first component is 2-methyl-6,7-dichloromelatonin.

29. A method according to claim 24, wherein said first component is β-methyl-6-fluoromelatonin.

30. A method according to claim 24, wherein said second component is tamoxifen.

31. A method according to claim 27, wherein said second component is tamoxifen.

32. A method according to claim 28, wherein said second component is tamoxifen.

33. A method according to claim 29, wherein said second component is tamoxifen.

34. A method according to claim 24, wherein said second component is an alkene derivative of the formula

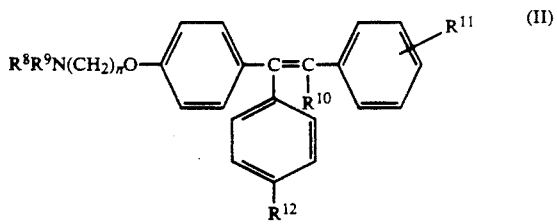

wherein
either $R^8$ is H or $C_1-C_4$ alkyl and $R^9$ is $C_1-C_4$ alkyl, or $R^8$ and $R^9$ are joined together with the adjacent nitrogen atom to form a heterocyclic radical, wherein said heterocyclic radical is a 5- or 6-membered nitrogen-containing ring structure optionally including an oxygen or sulfur atom as a second hetero-atom;
$R^{10}$ is H or $C_1-C_4$ alkyl;
$R^{11}$ is H, halo, OH, $C_1-C_4$ alkyl, or is a buta-1,3-dienyl radical such that together with the adjacent benzene ring forms a naphthyl radical;
$R^{12}$ is H or OH;
n is 2; or a pharmaceutically acceptable salt thereof.

35. A method according to claim 34, wherein
$R^8$ and $R^9$ of said alkene derivative are both the same $C_1-C_4$ alkyl group;
$R^{10}$ is $C_1-C_4$ alkyl;
$R^{11}$ is halo or $C_1-C_4$ alkyl;
$R^{12}$ is OH; and
n is 2.

36. A method according to claim 24, wherein said mammal is a human.

* * * * *

UNITED STATES PATENT AND TRADEMARK OFFICE
CERTIFICATE OF CORRECTION

PATENT NO. : 5,196,435
DATED : March 23, 1993
INVENTOR(S) : James A. Clemens, et al It is certified that error appears in the above-indentified patent and that said Letters Patent is hereby corrected as shown below:

Claim 10, column 11, line 32, "$R^2H$" should read --$R^2$ is H--.

Claim 10, column 11, line 37, "H and halo" should read --H or halo--.

Signed and Sealed this

Tenth Day of May, 1994

*Attest:*

BRUCE LEHMAN

*Attesting Officer*     *Commissioner of Patents and Trademarks*